United States Patent

Brunner et al.

(10) Patent No.: US 6,284,917 B1
(45) Date of Patent: Sep. 4, 2001

(54) METHOD FOR HYDROGENATING BENZENE POLYCARBOXYLIC ACIDS OR DERIVATIVES THEREOF BY USING A CATALYST CONTAINING MACROPORES

(75) Inventors: Melanie Brunner, Schifferstadt; Arnd Böttcher, Frankenthal; Boris Breitscheidel, Limburgerhof; Klaus Halbritter, Heidelberg; Jochem Henkelmann, Mannheim; Lucien Thil, Limburgerhof; Rolf Pinkos, Dürkheim, all of (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/581,843

(22) PCT Filed: Dec. 18, 1998

(86) PCT No.: PCT/EP98/08346

§ 371 Date: Jun. 19, 2000

§ 102(e) Date: Jun. 19, 2000

(87) PCT Pub. No.: WO99/32427

PCT Pub. Date: Jul. 1, 1999

(30) Foreign Application Priority Data

Dec. 19, 1997 (DE) ................................. 197 56 913
Jul. 16, 1998 (DE) ................................. 198 32 088

(51) Int. Cl.$^7$ .................................................. C07C 69/74
(52) U.S. Cl. ............................................................ 560/127
(58) Field of Search ............................................... 560/127

(56) References Cited

U.S. PATENT DOCUMENTS 2,070,770 * 2/1937 Amend .
5,286,898 * 2/1994 Gustafson et al. .................. 560/127

FOREIGN PATENT DOCUMENTS

06321823 A2 * 11/1994 (JP) .
WO 9932427 A1 * 7/1999 (WO) .

* cited by examiner

Primary Examiner—Ralph Gitomer
Assistant Examiner—Devesh Khare
(74) Attorney, Agent, or Firm—Herbert B. Keil

(57) ABSTRACT

A process for hydrogenating a benzenepolycarboxylic acid or a derivative thereof or a mixture of two or more thereof by bringing the benzenepolycarboxylic acid or the derivative thereof or the mixture of two or more thereof into contact with a hydrogen-containing gas is carried out in the presence of a catalyst which comprises as active metal at least one metal of transition group VIII of the Periodic Table alone or together with at least one metal of transition group I or VII of the periodic table applied to a support which contains macropores with the proviso that if dimethyl terephthalate is hydrogenated, the hydrogenation using a catalyst which comprises as active metal ruthenium either alone or together with at least one metal of transition group I, VII or VIII of the Periodic Table applied to a support, where the support has a mean pore diameter of at least 50 nm and a BET surface area of at most 30 $m^2/g$ and the amount of the active metal is from 0.01 to 30% by weight, based on the total weight of the catalyst, and the ratio of the surface areas of the active metal and the catalyst support is less than 0.05, and/or a catalyst which comprises as active metal ruthenium either alone or together with at least one metal of transition group I, VII or VIII of the Periodic Table in an amount of from 0.01 to 30% by weight, based on the total weight of the catalyst, applied to a support, where from 10 to 50% of the pore volume of the support is formed by macropores having a pore diameter in the range from 50 nm to 10,000 nm and from 50 to 90% of the pore volume of the support is formed by mesopores having a pore diameter in the range from 2 to 50 nm, where the sum of the pore volumes adds up to 100%, is excluded, and novel hydrogenation products, obtainable by hydrogenating benzenepolycarboxylic acid (derivatives) as well as their use as plasticizers in plastics.

21 Claims, No Drawings"

METHOD FOR HYDROGENATING BENZENE POLYCARBOXYLIC ACIDS OR DERIVATIVES THEREOF BY USING A CATALYST CONTAINING MACROPORES

The present invention relates to a process for hydrogenating benzenepolycarboxylic acids or derivatives thereof, such as esters and/or anhydrides, by bringing one or more benzenepolycarboxylic acids or one or more derivatives thereof into contact with a hydrogen-containing gas in the presence of a catalyst containing macropores.

Furthermore, the present invention also relates to selected products as obtained by the hydrogenation according to the invention as such, i.e. the corresponding cyclohexane compounds, in particular of cyclohexanedicarboxylic esters and cyclohexanetricarboxylic esters, in particular the cyclohexanedicarboxylic esters and cyclohexanetricarboxylic esters. Furthermore, the invention also relates to the use of the obtained cyclohexanedicarboxylic esters as plasticizers in plastics.

In U.S. Pat. No. 5,286,898 and U.S. Pat. No. 5,319,129, dimethyl terephthalate is hydrogenated at $\geq 140°$ C. and a pressure of from 50 to 170 bar over supported Pd catalysts which are treated with Ni, Pt and/or Ru to give the corresponding dimethyl hexahydroterephthalate. In DE-A 28 23 165, aromatic carboxylic esters are hydrogenated at from 70 to 250° C. and from 30 to 200 bar over supported Ni, Ru, Rh and/or Pd catalysts to give the corresponding cycloaliphatic carboxylic esters. U.S. Pat. No. 3,027,398 describes the hydrogenation of dimethyl terephthalate over supported Ru catalysts at from 110 to 140° C. and from 35 to 105 bar.

EP-A 0 603 825 relates to a process for the preparation of 1,4-cycylohexanedicarboxylic acid by hydrogenating terephthalic acid by using a supported palladium catalyst, wherein as support alumina, silica or active charcoal is used. The process described therein is particularly characterized in that the solution comprising an 1,4-cyclohexanedicarboxylic acid as obtained in a first step is brought into contact with steam, thereby leading to an extraction of the impurities as obtained in said solution. This process is, however, only applicable to acids, since when using it for derivatives, such as e.g. esters, anhydrides, etc. there exists the risk of hydrolysis. The use of a support comprising macropores is not mentioned in this application.

Up to now, predominantly phthalic acid esters, such as dibutyl, dioctyl or isononyl esters of phthalic acid have been used as plasticizers in plastics, such as PVC, as may be deduced from e.g. FR-A 2,397,131. However, since recently these compounds are regarded as being detrimental under health aspects and thus their use in plastics for producing e.g. tools for children is under an increasing criticism, in some countries their use is even forbidden.

The use of several cyclohexane-1,2-dicarboxylic acid esters as plasticizer is known from the prior art. Described is the use of cyclohexanedicarboxylic acid dimethyl or diethyl esters (DE-A 28 23 165), cyclohexane-1,2-dicarboxylic acid di(isononyl)ester (EP-A 07-011074) and cyclohexane-1,2-dicarboxylic acid di(2-ethylhexyl)ester (DE-A 12 63 296) as plasticizers in plastic.

It is an object of the present invention to provide a process for hydrogenating benzenepolycarboxylic acids or derivatives, in particular benzenedicarboxylic esters, using specific catalysts, by means of which the corresponding ring-hydrogenated derivatives, in particular cyclohexanedicarboxylic esters, can be obtained with a very high selectivity and in a very high space-time yield without significant secondary reactions.

A further object of the present invention lies in providing new products which are obtainable by the hydrogenation of benzenepolycarboxylic acid (derivatives) according to the invention, which should be preferably useable as plasticizers in plastics.

The present invention accordingly provides a process for hydrogenating a benzenepolycarboxylic acid or a derivative thereof or a mixture of two or more thereof by bringing the benzenepolycarboxylic acid or the derivative thereof or the mixture of two or more thereof into contact with a hydrogen-containing gas in the presence of a catalyst which comprises as active metal at least one metal of transition group VIII of the Periodic Table alone or together with at least one metal of transition group I or VIII of the periodic table applied to a support which contains macropores with the proviso that if dimethyl terephthalate is hydrogenated, the hydrogenation using a catalyst which comprises as active metal ruthenium either alone or together with at least one metal of transition group I, VII or VIII of the Periodic Table applied to a support, where the support has a mean pore diameter of at least 50 nm and a BET surface area of at most 30 $m^2/g$ and the amount of the active metal is from 0.01 to 30% by weight, based on the total weight of the catalyst, and the ratio of the surface areas of the active metal and the catalyst support is less than 0.05, or a catalyst which comprises as active metal ruthenium either alone or together with at least one metal of transition group I, VII or VIII of the Periodic Table in an amount of from 0.01 to 30% by weight, based on the total weight of the catalyst, applied to a support, where from 10 to 50% of the pore volume of the support is formed by macropores having a pore diameter in the range from 50 nm to 10,000 nm and from 50 to 90% of the pore volume of the support is formed by mesopores having a pore diameter in the range from 2 to 50 nm, where the sum of the pore volumes adds up to 100%, is excluded.

In a preferred embodiment, the present invention provides a process for hydrogenating a benzenepolycarboxylic acid or a derivative thereof or a mixture of two or more thereof, wherein the catalyst comprises as active metal at least one metal of transition group VIII of the Periodic Table either alone or together with at least one metal of transition group I or VII of the Periodic Table applied to a support, where the support has a mean pore diameter of at least 50 nm and a BET surface area of at most 30 $m^2/g$ and the amount of the active metal is from 0.01 to 30% by weight, based on the total weight of the catalyst (catalyst 1).

Furthermore, the present invention provides a process of this type in which the catalyst comprises as active metal at least one metal of transition group VIII of the Periodic Table either alone or together with at least one metal of transition group I or VII of the Periodic Table in an amount of from 0.01 to 30% by weight, based on the total weight of the catalyst, applied to a support, where from 10 to 50% of the pore volume of the support is formed by macropores having a pore diameter in the range from 50 nm to 10,000 nm and from 50 to 90% of the pore volume of the support is formed by mesopores having a pore diameter in the range from 2 to 50 nm, where the sum of the pore volumes adds up to 100% (catalyst 2).

In a further preferred embodiment, the present invention provides a process as defined above in which the catalyst (catalyst 3) comprises as active metal at least one metal of transition group VIII of the Periodic Table either alone or together with at least one metal of transition group I or VII of the Periodic Table in an amount of from 0.01 to 30% by weight, based on the total weight of the catalyst, applied to a support, where the support has a mean pore diameter of at least 0.1 μm and a BET surface area of at most 15 m²/g. Supports used can in principle be all supports which contain macropores, i.e. supports which contain only macropores as well as those which contain mesopores and/or micropores in addition to macropores.

Active metals which can be used are in principle all metals of transition group VIII of the Periodic Table. Preference is given to using platinum, rhodium, palladium, cobalt, nickel or ruthenium or a mixture of two or more thereof as active metal; particular preference is given to using ruthenium as active metal. Among the metals of transition group I or VII or else transition groups I and VII of the Periodic Table which are likewise all usable in principle, preference is given to using copper and/or rhenium.

For the purposes of the present invention, the terms "macropores" and "mesopores" are used as they are defined in *Pure Appl. Chem.*, 45 (1976), 79, namely as pores whose diameter is above 50 nm (macropores) or whose diameter is from 2 nm and 50 nm (mesopores).

The active metal content is generally from about 0.01 to about 30% by weight, preferably from about 0.01 to about 5% by weight and in particular from about 0.1 to about 5% by weight, in each case based on the total weight of the catalyst used; the contents preferably used in the preferred catalysts 1 to 3 described below will again be specified individually in the discussion of these catalysts.

The term "benzenepolycarboxylic acid or a derivative thereof" used for the purposes of the present invention encompasses all benzenepolycarboxylic acids as such, e.g. phthalic acid, isophthalic acid, terephthalic acid, trimellitic acid, trimesic acid, hemimellitic acid and pyromellitic acid, and derivatives thereof, particularly monoesters, diesters and possibly triesters and tetra-esters, in particular alkyl esters, and anhydrides. The compounds which are preferably used will be briefly described once more in the section "Method of carrying out the process" below.

The catalysts 1 to 3 which are preferably used will now be described in detail below. In the description, ruthenium is used as active metal by way of example, but the statements made below are also applicable to the other active metals which can be used, as defined herein.

Catalyst 1

The catalysts 1 used according to the present invention can be produced industrially by applying at least one metal of transition group VIII of the Periodic Table and, if desired, at least one metal of transition group I or VII of the Periodic Table to a suitable support.

The metal(s) can be applied by steeping the support in aqueous metal salt solutions such as aqueous ruthenium salt solutions, by spraying appropriate metal salt solutions onto the support or by other suitable methods. Suitable metal salts of transition group I, VII or VIII of the Periodic Table are the nitrates, nitrosyl nitrates, halides, carbonates, carboxylates, acetylacetonates, chloro complexes, nitrito complexes or ammine complexes of the corresponding metals, with preference being given to the nitrates and nitrosyl nitrates.

In the case of metals which have not only a metal of transition group VIII of the Periodic Table but also further metals applied as active metals to the support, the metal salts or metal salt solutions can be applied simultaneously or in succession.

The supports which have been coated or impregnated with the metal salt solution are subsequently dried, preferably at from 100 to 150° C., and, if desired, calcined at from 200 to 600° C., preferably from 350 to 450° C. In the case of separate impregnation, the catalyst is dried and, if desired, calcined as described above after each impregnation step. The order in which the support is impregnated with the active components is immaterial.

The coated and dried and, if desired, calcined supports are subsequently activated by treatment in a gas stream comprising free hydrogen at from about 30 to about 600° C., preferably from about 150 to about 450° C. The gas stream preferably consists of from 50 to 100% by volume of $H_2$ and from 0 to 50% by volume of $N_2$.

The metal salt solution or solutions are applied to the support or supports in such an amount that the total active metal content, in each case based on the total weight of the catalyst, is from about 0.01 to about 30% by weight, preferably from about 0.01 to about 5% by weight, more preferably from about 0.01 to about 1% by weight and in particular from about 0.05 to about 1% by weight.

The total metal surface area on the catalyst 1 is preferably from about 0.01 to about 10 m²/g, more preferably from about 0.05 to about 5 m²/g and in particular from about 0.05 to about 3 m²/g of the catalyst. The metal surface area is determined by means of the chemisorption method described by J. Lemaitre et al. in *"Characterization of Heterogenous Catalysts"*, edited by Francis Delanney, Marcel Dekker, New York 1984, pp. 310–324.

In the catalyst 1 used according to the present invention, the ratio of the surface areas of the active metal/metals and the catalyst support is preferably less than about 0.05, with the lower limit being about 0.0005.

The support materials which can be used for producing the catalysts used according to the present invention are those which are macroporous and have a mean pore diameter of at least about 50 nm, preferably at least about 100 nm, in particular at least about 500 nm, and whose BET surface area is at most about 30 m²/g, preferably at most about 15 m²/g, more preferably at most about 10 m²/g, in particular at most about 5 m²/g and more preferably at most about 3 m²/g. The mean pore diameter of the support is preferably from about 100 nm to about 200 μm, more preferably from about 500 nm to about 50 μm. The surface area of the support is preferably from about 0.2 to about 15 m²/g, more preferably from about 0.5 to about 10 m²/g, in particular from about 0.5 to about 5 m²/g and more preferably from about 0.5 to about 3 m²/g.

The surface area of the support is determined by the BET method using $N_2$ adsorption, in particular in accordance with DIN 66131. The mean pore diameter and the pore size distribution are determined by Hg porosimetry, in particular in accordance with DIN 66133.

The pore size distribution of the support is preferably approximately bimodal, with the pore diameter distribution having maxima at about 600 nm and about 20 μm in the bimodal distribution representing a specific embodiment of the invention.

Further preference is given to a support which has a surface area of 1.75 m²/g and this bimodal distribution of the pore diameter. The pore volume of this preferred support is preferably about 0.53 ml/g.

Macroporous support materials which can be used are, for example, macropores containing activated carbon, silicon carbide, aluminum oxide, silicon dioxide, titanium dioxide, zirconium dioxide, magnesium oxide, zinc oxide or mixtures of two or more thereof, with preference being given to using aluminum oxide and zirconium dioxide.

Further details regarding catalyst 1 or its production may be found in DE-A 196 24 484.6, whose entire contents on this subject are incorporated by reference into the present application.

Catalyst 2

The catalysts 2 used according to the present invention comprise one or more metals of transition group VIII of the Periodic Table as active component(s) on a support as defined herein. Preference is given to using ruthenium, palladium and/or rhodium as active component(s).

The catalysts 2 used according to the present invention can be produced industrially by application of an active metal of transition group VIII of the Periodic Table, preferably ruthenium or palladium, and, if desired, at least one metal of transition group I or VII of the Periodic Table to a suitable support. The application can be achieved by steeping the support in aqueous metal salt solutions, for example ruthenium or palladium salt solutions, by spraying appropriate metal salt solutions onto the support or by other suitable methods. Suitable metal salts for preparing the metal salt solutions are the nitrates, nitrosyl nitrates, halides, carbonates, carboxylates, acetylacetonates, chloro complexes, nitrito complexes or ammine complexes of the corresponding metals, with preference being given to the nitrates and nitrosyl nitrates.

In the case of catalysts which have a plurality of active metals applied to the support, the metal salts or metal salt solutions can be applied simultaneously or in succession.

The supports which have been coated or impregnated with the metal salt solution are subsequently dried, preferably at from 100 to 150° C. If desired, these supports can be calcined at from 200 to 600° C., preferably from 350 to 450° C. The coated supports are subsequently activated by treatment in a gas stream comprising free hydrogen at from 30 to 600° C., preferably from 100 to 450° C., and in particular from 100 to 300° C. The gas stream preferably consists of from 50 to 100% by volume of $H_2$ and from 0 to 50% by volume of $N_2$.

If a plurality of active metals are applied to the support and the application is carried out in succession, the support can be dried at from 100 to 150° C. and, if desired, calcined at from 200 to 600° C. after each application or impregnation. The order in which the metal salt solution is applied to the support or the support is impregnated with the metal salt solution is immaterial.

The metal salt solution is applied to the support(s) in such an amount that the active metal content is from 0.01 to 30% by weight, preferably from 0.01 to 10% by weight, more preferably from 0.01 to 5% by weight, and in particular from 0.3 to 1% by weight, based on the total weight of the catalyst.

The total metal surface area on the catalyst is preferably from 0.01 to 10 $m^2/g$, particularly preferably from 0.05 to 5 $m^2/g$ and more preferably from 0.05 to 3 $m^2/g$ of the catalyst. The metal surface area is measured by the chemisorption method as described in J. Lemaitre et al., "*Characterization of Heterogenous Catalysts*", edited by Francis Delanney, Marcel Dekker, New York (1984), pp. 310–324.

In the catalyst 2 used according to the present invention, the ratio of the surface areas of the active metal or metals and the catalyst support is less than about 0.3, preferably less than about 0.1 and in particular about 0.05 or less, with the lower limit being about 0.0005.

The support materials which can be used for producing the catalysts 2 used according to the present invention possess macropores and mesopores.

The supports which can be used according to the present invention have a pore distribution in which from about 5 to about 50%, preferably from about 10 to about 45%, more preferably from about 10 to about 30 and in particular from about 15 to about 25%, of the pore volume is formed by macropores having pore diameters in the range from about 50 nm to about 10,000 nm and from about 50 to about 95%, preferably from about 55 to about 90%, more preferably from about 70 to about 90% and in particular from about 75 to about 85%, of the pore volume is formed by mesopores having a pore diameter of from about 2 to about 50 nm where in each case the sum of the pore volumes adds up to 100%.

The total pore volume of the supports used according to the present invention is from about 0.05 to 1.5 $cm^3/g$, preferably from 0.1 to 1.2 $cm^3/g$ and in particular from about 0.3 to 1.0 $cm^3/g$. The mean pore diameter of the supports used according to the present invention is from about 5 to 20 nm, preferably from about 8 to about 15 nm and in particular from about 9 to about 12 nm.

The surface area of the support is preferably from about 50 to about 500 $m^2/g$, more preferably from about 200 to about 350 $m^2/g$ and in particular from about 250 to about 300 $m^2/g$ of the support.

The surface area of the support is determined by the BET method using $N_2$ adsorption, in particular in accordance with DIN 66131. The mean pore diameter and the size distribution are determined by Hg porosimetry, in particular in accordance with DIN 66133.

Although all support materials known in catalyst production, i.e. those which have the above-defined pore size distribution, can be used in principle, preference is given to using macropores containing activated carbon, silicon carbide, aluminum oxide, silicon dioxide, titanium dioxide, zirconium dioxide, magnesium oxide, zinc oxide or mixtures thereof, more preferably aluminum oxide and zirconium dioxide.

Further details regarding catalyst 2 or its production may be found in DE-A 196 24 485.4, whose entire contents on this subject are incorporated by reference into the present application.

Catalyst 3

The catalysts 3 used according to the present invention can be produced industrially by application of an active metal of transition group VIII of the Periodic Table and, if desired, at least one metal of transition group I or VII of the Periodic Table to a suitable support. The application can be achieved by steeping the support in aqueous metal salt solutions such as ruthenium salt solutions, by spraying appropriate metal salt solutions onto the support or by other suitable methods. Salts which are suitable as ruthenium salts for preparing the ruthenium salt solutions and as metal salts of transition group I, VII or VIII are the nitrates, nitrosyl nitrates, halides, carbonates, carboxylates, acetylacetonates, chloro complexes, nitrito complexes or ammine complexes of the corresponding metals; preference is given to the nitrates and nitrosyl nitrates.

In the case of catalysts which comprise a plurality of metals applied to the support, the metal salts or metal salt solutions can be applied simultaneously or in succession.

The supports coated or impregnated with the ruthenium salt or metal salt solution are then dried, preferably at from 100 to 150° C., and, if desired calcined at from 200 to 600° C.

The coated supports are subsequently activated by treating the coated supports in a gas stream comprising free hydrogen at from 30 to 600° C., preferably from 150 to 450° C. The gas stream preferably consists of from 50 to 100% by volume of $H_2$ and from 0 to 50% by volume of $N_2$.

If both the active metal of transition group VIII of the Periodic Table and metals of transition group I or VII are applied to the support and the application is carried out in succession, the support can be dried at from 100 to 150° C. and, if desired, calcined at from 200 to 600° C. after each application or impregnation. The order in which the metal salt solutions are applied or the support is impregnated with them is immaterial.

The metal salt solution is applied to the support(s) in such an amount that from 0.01 to 30% by weight, based on the total weight of the catalyst, of active metal are present on the support. This amount is preferably from 0.2 to 15% by weight, particularly preferably about 0.5% by weight.

The total metal surface area on the catalyst 3 is preferably from 0.01 to 10 $m^2/g$, particularly preferably from 0.05 to 5 $m^2/g$, in particular from 0.05 to 3 $m^2$ per g of the catalyst.

The support materials which can be used for producing the catalysts 3 used according to the present invention are preferably ones which are macroporous and have a mean pore diameter of at least 0.1 lm, preferably at least 0.5 lm, and a surface area of at most 15 $m^2/g$, preferably at most 10 $m^2/g$, particularly preferably at most 5 $m^2/g$, in particular at most 3 $m^2/g$. The mean pore diameter of the support is preferably in a range from 0.1 to 200 lm, in particular from 0.5 to 50 lm. The surface area of the support is preferably from 0.2 to 15 $m^2/g$, particularly preferably from 0.5 to 10 $m^2/g$, in particular from 0.5 to 5 $m^2/g$, especially from 0.5 to 3 $m^2/g$ of the support.

The surface area of the support is determined by the BET method using $N_2$ adsorption, in particular in accordance with DIN 66131. The mean pore diameter and the pore size distribution are determined by Hg porosimetry, in particular in accordance with DIN 66133. The pore size distribution of the support is preferably approximately bimodal, with the pore diameter distribution having maxima at about 0.6 lm and about 20 lm in the bimodal distribution representing a specific embodiment of the invention.

Particular preference is given to a support having a surface area of about 1.75 $m^2/g$ and having this bimodal distribution of the pore diameter. The pore volume of this preferred support is preferably about 0.53 ml/g.

Macroporous support materials which can be used are, for example, macropores containing activated carbon, silicon carbide, aluminum oxide, silicon dioxide, titanium dioxide, zirconium dioxide, magnesium oxide, zinc oxide or mixtures thereof. Preference is given to aluminum oxide and zirconium dioxide.

Further details regarding catalyst 3 or its production may be found in DE-A 196 04 791.9, whose entire contents on this subject are incorporated by reference into the present application.

Method of Carrying Out the Process

In the process of the present invention, the hydrogenation is generally carried out at from about 50 to 250° C., preferably from about 70 to 220° C. The pressures used here are generally above 10 bar, preferably from about 20 to about 300 bar.

The process of the present invention can be carried out either continuously or batchwise, with preference being given to carrying out the process continuously.

When the process is carried out continuously, the amount of the benzenepolycarboxylic acid or ester to be hydrogenated or of the mixture of two or more thereof is preferably from about 0.05 to about 3 kg per liter of catalyst per hour, more preferably from about 0.1 to about 1 kg per liter of catalyst per hour.

As hydrogenation gases, it is possible to use any gases which comprise free hydrogen and do not contain harmful amounts of catalyst poisons such as CO. For example, waste gases from a reformer can be used. Preference is given to using pure hydrogen as hydrogenation gas.

The hydrogenation of the present invention can be carried out in the presence or absence of a solvent or diluent, i.e. it is not necessary to carry out the hydrogenation in solution.

However, preference is given to using a solvent or diluent. Solvents or diluents which can be used are any suitable solvent or diluent. The choice is not critical as long as the solvent or diluent used is able to form a homogeneous solution with the benzenepolycarboxylic acid or ester to be hydrogenated. For example, the solvents or diluents can also comprise water.

Examples of suitable solvents or diluents include the following:

straight-chain or cyclic ethers such as tetrahydrofuran or dioxane, and also aliphatic alcohols in which the alkyl radical preferably has from 1 to 10 carbon atoms, in particular from 3 to 6 carbon atoms.

Examples of alcohols which are preferably used are i-propanol, n-butanol, i-butanol and n-hexanol.

Mixtures of these or other solvents or diluents can likewise be used.

The amount of solvent or diluent used is not restricted in any particular way and can be selected freely depending on requirements. However, preference is given to amounts which lead to a 10–70% strength by weight solution of the benzenepolycarboxylic acid or ester to be hydrogenated.

In the process of the present invention, particular preference is given to using the product formed in the hydrogenation, i.e. the corresponding cyclohexane derivative, as solvent, if desired in addition to other solvents or diluents. In any case, part of the product formed in the process can be mixed with the benzenepolycarboxylic acid still to be hydrogenated or the derivative thereof The amount of reaction product which is mixed in as solution or diluent is preferably from 1 to 30 times, particularly preferably from 5 to 20 times, in particular from 5 to 10 times, the weight of the compound to be hydrogenated.

As mentioned above, the term "benzenepolycarboxylic acids or derivatives thereof" used for the purposes of the present invention encompasses both the respective benzenepolycarboxylic acids as such and derivatives thereof, particularly monoesters, diesters or possibly triesters or tetraesters and also anhydrides of the benzenepolycarboxylic acids. The esters used are alkyl, cycloalkyl and alkoxyalkyl esters, where the alkyl, cycloalkyl and alkoxyalkyl groups generally have from 1 to 30, preferably from 2 to 20 and particularly preferably from 3 to 18, carbon atoms and can be branched or linear.

Specific examples are:

alkyl terephthalates such as monomethyl terephthalate, dimethyl terephthalate, diethyl terephthalate, di-n-propyl terephthalate, di-n-butyl terephthalate, di-tert-butyl terephthalate, diisobutyl terephthalate, monoglycol esters of terephthalic acid, diglycol esters of terephthalic acid, di-n-octyl terephthalate, diisooctyl terephthalate, mono-2-ethylhexyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisododecyl terephthalate, di-n-octadecyl terephthalate, diisooctadecyl terephthalate, di-n-eicosyl terephthalate, monocyclohexyl terephthalate, dicyclohexyl terephthalate;

alkyl phthalates such as monomethyl phthalate, dimethyl phthalate, diethyl phthalate, di-n-propyl phthalate, di-n-butyl phthalate, di-tert-butyl phthalate, diisobutyl phthalate, monoglycol esters of phthalic acid, diglycol esters of phthalic acid, di-n-octyl phthalate, diisooctyl phthalate, di-2-ethylhexyl phthalate, di-n-nonyl phthalate, diisononyl phthalate, di-n-decyl phthalate, diisodecyl phthalate, di-n-undecyl phthalate, diisododecyl phthalate, di-n-octadecyl phthalate, diisooctadecyl phthalate, di-n-eicosyl phthalate, monocyclohexyl phthalate, dicyclohexyl phthalate;

alkyl isophthalates such as monomethyl isophthalate, dimethyl isophthalate, diethyl isophthalate, di-n-propyl isophthalate, di-n-butyl isophthalate, di-tert-butyl isophthalate, diisobutyl isophthalate, monoglycol esters of isophthalic acid, diglycol esters of isophthalic acid, di-n-octyl isophthalate, diisooctyl isophthalate, di-2-ethylhexyl isophthalate, di-n-nonyl isophthalate, diisononyl isophthalate, di-n-decyl isophthalate, diisodecyl isophthalate, di-n-undecyl isophthalate, diisododecyl isophthalate, di-n-octadecyl isophthalate, diisooctadecyl isophthalate, di-n-eicosyl isophthalate, monocyclohexyl isophthalate, dicyclohexyl isophthalate;

Alkyl trimellitates such as monomethyl trimellitate, dimethyl trimellitate, diethyl trimellitate, di-n-propyl trimellitate, di-n-butyl trimellitate, di-tert-butyl trimellitate, diisobutyl trimellitate, the monoglycol ester of trimellitic acid, diglycol esters of trimellitic acid, di-n-octyl trimellitate, diisooctyl trimellitate, di-2-ethylhexyl trimellitate, di-n-nonyl trimellitate, diisononyl trimellitate, di-n-decyl trimellitate, diisodecyl trimellitate, di-n-undecyl trimellitate, diisododecyl trimellitate, di-n-octadecyl trimellitate, diisooctadecyl trimellitate, di-n-eicosyl trimellitate, monocyclohexyl trimellitate, dicyclohexyl trimellitate and trimethyl trimellitate, triethyl trimellitate, tri-n-propyl trimellitate, tri-n-butyl trimellitate, tri-tert-butyl trimellitate, triisobutyl trimellitate, triglycol esters of trimellitic acid, tri-n-octyl trimellitate, triisooctyl trimellitate, tri-2-ethylhexyl trimellitate, tri-n-nonyl trimellitate, triisododecyl trimellitate, tri-n-undecyl trimellitate, triisododecyl trimellitate, tri-n-octadecyl trimellitate, triisooctadecyl trimellitate, tri-n-eicosyl trimellitate, tricyclohexyl trimellitate;

alkyl trimesates such as monomethyl trimesate, dimethyl trimesate, diethyl trimesate, di-n-propyl trimesate, di-n-butyl trimesate, di-tert-butyl trimesate, diisobutyl trimesate, monoglycol esters of trimesic acid, diglycol esters of trimesic acid, di-n-octyl trimesate, diisooctyl trimesate, di-2-ethylhexyl trimesate, di-n-nonyl trimesate, diisononyl trimesate, di-n-decyl trimesate, diisodecyl trimesate, di-n-undecyl trimesate, diisododecyl trimesate, di-n-octadecyl trimesate, diisooctadecyl trimesate, di-n-eicosyl trimesate, monocyclohexyl trimesate, dicyclohexyl trimesate, and also trimethyl trimesate, triethyl trimesate, tri-n-propyl trimesate, tri-n-butyl trimesate, tri-tert-butyl trimesate, triisobutyl trimesate, triglycol esters of trimesic acid, tri-n-octyl trimesate, triisooctyl trimesate, tri-2-ethyl-hexyl trimesate, tri-n-nonyl trimesate, triisododecyl trimesate, tri-n-undecyl trimesate, triisododecyl trimesate, tri-n-octadecyl trimesate, triisooctadecyl trimesate, tri-n-eicosyl trimesate, tricyclohexyl trimesate;

alkyl hemimellitates such as monomethyl hemimellitate, dimethyl hemimellitate, diethyl hemimellitate, di-n-propyl hemimellitate, di-n-butyl hemimellitate, di-tert-butyl hemimellitate, diisobutyl hemimellitate, monoglycol esters of hemimellitic acid, diglycol esters of hemimellitic acid, di-n-octyl hemimellitate, diisooctyl hemimellitate, di-2-ethylhexyl hemimellitate, di-n-nonyl hemimellitate, diisononyl hemimellitate, di-n-decyl hemimellitate, diisodecyl hemimellitate, di-n-undecyl hemimellitate, diisododecyl hemimellitate, di-n-octadecyl hemimellitate, diisooctadecyl hemimellitate, di-n-eicosyl hemimellitate, monocyclohexyl hemimellitate, dicyclohexyl hemimellitate, and also trimethyl hemimellitate, triethyl hemimellitate, tri-n-propyl hemimellitate, tri-n-butyl hemimellitate, tri-tert-butyl hemimellitate, triisobutyl hemimellitate, triglycol esters of hemimellitic acid, tri-n-octyl hemimellitate, triisooctyl hemimellitate, tri-2-ethylhexyl hemimellitate, tri-n-nonyl hemimellitate, triisododecyl hemimellitate, tri-n-undecyl hemimellitate, triisododecyl hemimellitate, tri-n-octadecyl hemimellitate, triisooctadecyl hemimellitate, tri-n-eicosyl hemimellitate, tricyclohexyl hemimellitate;

alkyl pyromellitates such as monomethyl pyromellitate, dimethyl pyromellitate, diethyl pyromellitate, di-n-propyl pyromellitate, di-n-butyl pyromellitate, di-tert-butyl pyromellitate, diisobutyl pyromellitate, monoglycol esters of pyromellitic acid, diglycol esters of pyromellitic acid, di-n-octyl pyromellitate, diisooctyl pyromellitate, di-2-ethylhexyl pyromellitate, di-n-nonyl pyromellitate, diisononyl pyromellitate, di-n-decyl pyromellitate, diisodecyl pyromellitate, di-n-undecyl pyromellitate, diisododecyl pyromellitate, di-n-octadecyl pyromellitate, diisooctadecyl pyromellitate, di-n-eicosyl pyromellitate, monocyclohexyl pyromellitate, trimethyl pyromellitate, triethyl pyromellitate, tri-n-propyl pyromellitate, tri-n-butyl pyromellitate, tri-tert-butyl pyromellitate, triisobutyl pyromellitate, triglycol esters of pyromellitic acid, tri-n-octyl pyromellitate, triisooctyl pyromellitate, tri-2-ethylhexyl pyromellitate, tri-n-nonyl pyromellitate, triisododecyl pyromellitate, tri-n-undecyl pyromellitate, triisododecyl pyromellitate, tri-n-octadecyl pyromellitate, triisooctadecyl pyromellitate, tri-n-eicosyl pyromellitate, tricyclohexyl pyromellitate, and also tetramethyl pyromellitate, tetraethyl pyromellitate, tetra-n-propyl pyromellitate, tetra-n-butyl pyromellitate, tetra-tert-butyl pyromellitate, tetraisobutyl pyromellitate, tetraglycol esters of pyromellitic acid, tetra-n-octyl pyromellitate, tetraisooctyl pyromellitate, tetra-2-ethylhexyl pyromellitate, tetra-n-nonyl pyromellitate, tetraisododecyl pyromellitate, tetra-n-undecyl pyromellitate, tetraisododecyl pyromellitate, tetra-n-octadecyl pyromellitate, tetraisooctadecyl pyromellitate, tetra-n-eicosyl pyromellitate, tetracyclohexyl pyromellitate;

anhydrides of phthalic acid, trimellitic acid, hemimellitic acid and pyromellitic acid.

Of course, it is also possible to use mixtures of two or more of these compounds.

The products as obtained according to the invention are the corresponding cyclohexanepolycarboxylic acids or cyclohexanepoycarboxylic acid derivatives.

Furthermore, the present invention relates to the following new cyclohexanepolycarboxylic acids or cyclohexanpolycarboxylic acid derivatives as such:

cyclohexane-1,2-dicarboxylic acid di(isopentyl) ester, obtainable by hydrogenation of a di(isopentyl)phthalate having the Chemical Abstracts registry number (in the following: CAS No.) 84777-06-0;

cyclohexane-1,2-dicarboxylic acid di(isoheptyl) ester, obtainable by hydrogenating the di(isoheptyl)phthalate having the CAS No. 71888-89-6;

cyclohexane-1,2-dicarboxylic acid di(isononyl) ester, obtainable by hydrogenating the di(isononyl)phthalate having the CAS No. 68515-48-0;

cyclohexane-1,2-dicarboxylic acid di(isononyl) ester, obtainable by hydrogenating the di(isononyl)phthalate having the CAS No. 28553-12-0, which is based on n-butene;

cyclohexane-1,2-dicarboxylic acid di(isononyl) ester, obtainable by hydrogenating the di(isononyl)phthalate having the CAS No. 28553-12-0, which is based on isobutene;

a 1,2-di-$C_9$-ester of cyclohexanedicarboxylic acid, obtainable by hydrogenating the di(nonyl)phthalate having the CAS No. 68515-46-8;

cyclohexane-1,2-dicarboxylic acid di(isodecyl) ester, obtainable by hydrogenating a di(isodecyl)phthalate having the CAS No. 68515-49-1;

1,2-$C_{7-11}$-ester of cyclohexanedicarboxylic acid, obtainable by hydrogenating the corresponding phthalic acid ester having the CAS No. 68515-42-4;

1,2-di-$C_{7-11}$-ester of cyclohexanedicarboxylic acid, obtainable by hydrogenating the di-$C_{7-11}$-phthalates having the following CAS Nos.:

111381-89-6, 111381-90-9, 111381-91-0, 68515-44-6, 68515-45-7 and 3648-20-7;

a 1,2-di-$C_{9-11}$-ester of cyclohexanedicarboxylic acid, obtainable by hydrogenating a di-$C_{9-11}$-phthalate having the CAS No. 98515-43-5;

a 1,2-di(isodecyl)cyclohexanedicarboxylic acid ester, obtainable by hydrogenating a di(isodecyl)phthalate, consisting essentially of di-(2-propylheptyl)phthalate;

1,2-di-$C_{7-9}$-cyclohexanedicarboxylic acid ester, obtainable by hydrogenating the corresponding phthalic acid ester, which comprises branched and linear $C_{7-9}$-alkylester groups; respective phthalic acid esters which may be e.g. used as starting materials have the following CAS Nos.:

di-$C_{7-9}$-alkylphthalate having the CAS No. 111 381-89-6;

di-$C_7$-alkylphthalate having the CAS No. 68515-44-6; and di-$C_9$-alkylphthalate having the CAS No. 68515-45-7.

Furthermore, the present invention also provides for the use of cyclohexanepolycarboxylic esters, in particular the cyclohexanepolycarboxylic esters obtained using the process of the present invention, as plasticizers in plastics. Here, preference is generally given to diesters and triesters containing alkyl groups having from 3 to 18 carbon atoms and particular preference is given to the abovementioned, individually listed esters having from 3 to 18 carbon atoms.

More preferably, the above explicitly mentioned new $C_5$-, $C_7$-, $C_9$-, $C_{10}$-, $C_{7-11}$-, $C_{9-11}$- and $C_{7-9}$-esters of 1,2-cyclohexanedicarboxylic acids, as being obtainable by hydrogenating the corresponding phthalates and more preferably the hydrogenation products of the commercially available benzenepolycarboxylic acid esters with the trade names Jayflex DINP (CAS No. 68515-48-0), Jayflex DIDP (CAS No. 68515-49-1), Palatinol 9-P, Vestinol 9 (CAS No. 28553-12-0), TOTM-I (CAS No. 3319-31-1), Linplast 68-TM and Palatinol N (CAS No. 28553-12-0) are used as plasticizers in plastics. Among those is in tun preferred to use these compounds or mixtures thereof as plasticizers in mass plastics, such as e.g. PVC and polyolefins, such as polyethylene, polypropylene, polyisoprene and copolymers of ethylene or propylene and 1-butene, 1-hexene and 1-octene.

Compared to the until now predominantly phthalates as used as plasticizers, the cyclohexanepolycarboxylic acid (derivatives), as used according to the invention, exhibit a lower density and viscosity and lead to e.g. an improvement of the flexibility at low temperatures (Kälteflexibilität) of the plastic when compared with the usage of the corresponding phthalates as plasticizers, while properties such as shore A hardness and the mechanical properties of the resulting plastics are identical to those as resulting from the usage of phthalates. Furthermore, the cyclohexanepolycarboxylic acid (derivative)s according to the invention exhibit an improved process ability in the dry blend and as a result thereof a higher production speed. In the Plastisol processing by exhibit advantages attributed to the lower viscosity when compared with conventional phthalates.

The process of the present invention is illustrated below by means of some examples.

EXAMPLES

Examples of Catalyst Production

A mesoporous/macroporous aluminum oxide support which was in the form of 4 mm extrudates and had a BET surface area of 238 $m^2/g$ and a pore volume of 0.45 ml/g was impregnated with an aqueous ruthenium(III) nitrate solution having a concentration of 0.8% by weight. 0.15 ml/g (about 33% of the total volume) of the pores of the support had a diameter in the range from 50 nm to 10,000 nm and 0.30 ml/g (about 67% of the total pore volume) of the pores of the support had a pore diameter in the range from 2 to 50 nm. The volume of solution taken up by the support during impregnation corresponded approximately to the pore volume of the support used.

The support which had been impregnated with the ruthenium(III) nitrate solution was subsequently dried at 120° C. and activated (reduced) at 200° C. in a stream of hydrogen. The catalyst produced in this way contained 0.05% by weight of ruthenium, based on the weight of the catalyst.

Example 1

In a 300 ml pressure reactor, 10 g of the Ru catalyst as described in the example of catalyst production were placed in a catalyst basket insert and 197 g (0.5 mol) of diisooctyl phthalate were added. The hydrogenation was carried out using pure hydrogen at 80° C. and a constant pressure of 200 bar. Hydrogenation was continued until no more hydrogen was taken up (4 h). The reactor was subsequently vented. The conversion of the diisooctyl phthalate was 100%. The yield of diisooctyl hexahydrophthalate was 99.7%, based on the total amount of diisooctyl phthalate used.

Example 2

In a 300 ml pressure reactor, 10 g of the Ru catalyst were placed in a catalyst basket insert and 194 g (0.46 mol) of diisononyl phthalate were added. The hydrogenation was carried out using pure hydrogen at 80° C. and a constant pressure of 100 bar. Hydrogenation was continued until no more hydrogen was taken up (10 h). The reactor was subsequently vented. The conversion of diisononyl phthalate was 100%. The yield of diisononyl hexahydrophthalate was 99.5%, based on the total amount of diisononyl phthalate used.

Example 3

In a 300 ml pressure reactor, 10 g of the Ru catalyst as described in the example of catalyst production were placed in a catalyst basket insert and 195 g (0.39 mol) of diisododecyl phthalate were added. The hydrogenation was carried out using pure hydrogen at 80° C. and a constant pressure of 200 bar. Hydrogenation was continued until no more hydrogen was taken up (4 h). The reactor was subsequently vented. The conversion of diisododecyl phthalate was 100%. The yield of diisododecyl hexahydrophthalate was 99.5%, based on the total amount of diisododecyl phthalate used.

Example 4

In a 300 ml pressure reactor, 10 g of the Ru catalyst were placed in a catalyst basket insert and 38.4 g (0.2 mol) of dimethyl isophthalate, dissolved in 100 g of THF, were added. The hydrogenation was carried out using pure hydrogen at 80° C. and a constant pressure of 200 bar. Hydrogenation was continued until no more hydrogen was taken up and the reactor was subsequently vented. The conversion of dimethyl isophthalate was 95.3%. The yield of dimethyl hexahydroisophthalate was 95.3%.

Example 5

In a 300 ml pressure reactor, 10 g of the Ru catalyst were placed in a catalyst basket insert and 25.2 g (0.1 mol) of trimethyl trimesate, dissolved in 100 g of THF, were added. The hydrogenation was carried out using pure hydrogen at 120° C. and a constant pressure of 200 bar. Hydrogenation was continued until no more hydrogen was taken up and the reactor was subsequently vented. The conversion of trimethyl trimesate was 97%. The yield of trimethyl hexahydrotrimesate was 93%.

Example 6

In a 300 ml pressure reactor, 10 g of the Ru catalyst were placed in a catalyst basket insert and 25.2 g (0.1 mol) of trimethyl trimellitate, dissolved in 100 g of THF, were added. The hydrogenation was carried out using pure hydrogen at 120° C. and a constant pressure of 200 bar. Hydrogenation was continued until no more hydrogen was taken up and the reactor was subsequently vented. The conversion of trimethyl trimellitate was 35%. The yield of trimethyl hexahydrotrimellitate was 33%.

Example 7

In a 300 ml pressure reactor, 10 g of the Ru catalyst were placed in a catalyst basket insert and 10.0 g (0.03 mol) of tetramethyl pyromellitate, dissolved in 100 g of THF, were added. The hydrogenation was carried out using pure hydrogen at 80° C. and a constant pressure of 200 bar. Hydrogenation was continued until no more hydrogen was taken up and the reactor was subsequently vented. The conversion of tetramethyl pyromellitate was 45%. The yield of tetramethyl hexahydropyromellitate was 44%.

Example 8

In a 1.2 l pressure reactor, 53 g of the supported Ru catalyst were placed in a catalyst basket insert and 800 g (1.9 mol) Jayflex DINP (CAS No. 68515-48-0) were added. The hydrogenation was carried out using pure hydrogen at 80° C. and a constant pressure of 200 bar. Hydrogenation was continued until no more hydrogen was taken up (6 h) and the reactor was subsequently vented. The conversion of Jayflex DINP was 100%. The yield of the corresponding cyclohexanedicarboxylic acid ester was 99.5%, relative to the total amount of the added Jayflex DINP.

Example 9

In a 0.3 l pressure reactor, 10 g of the supported Ru catalyst were placed in a catalyst basket insert and 150 g (0.35 mol) Palatinol 9-P were added. The hydrogenation was carried out using pure hydrogen at a temperature of 120° C. and a constant pressure of 200 bar. Hydrogenation was continued until no more hydrogen was taken up (2 h) and the reactor was subsequently vented. The conversion of Palatinol 9-P (1,2-di(nonyl, linear and branched) benzenedicarboxylic acid ester) was 100%. The yield of the corresponding cyclohexanedicarboxylic acid ester was 99.4%, relative to the total amount of the used Palatinol 9-P.

Example 10

In a 1.2 l pressure reactor, 53 g of the supported Ru catalyst were placed in a catalyst basket insert and 780 g (1.87 mol) Vestinol 9 (CAS No. 28553-12-0) were added. The hydrogenation was carried out using pure hydrogen at a temperature of 120° C. and a constant pressure of 200 bar. Hydrogenation was continued until no more hydrogen was taken up (4 h) and the reactor was subsequently vented. The conversion of the corresponding cyclohexanedicarboxylic acid ester was 99.4%, relative to the total amount of the used Vestinol 9.

Example 11

In a 1.2 l pressure reactor, 53 g of the supported Ru catalyst were placed in a catalyst basket insert and 760 g (1.7 mol) Jayflex DIDP (CAS No. 68515-49-1) were added. The hydrogenation was carried out using pure hydrogen at 80° C. and a constant pressure of 200 bar. Hydrogenation was continued until no more hydrogen was taken up (10 h) and the reactor was subsequently vented. The conversion of Jayflex DIDP was 100%. The yield of the corresponding cyclohexanedicarboxylic acid ester was 99.5%, relative to the total amount of the used Jayflex DIDP.

Example 12

In a 1.2 l pressure reactor, 53 g of the supported Ru catalyst were placed in a catalyst basket insert and 800 g (1.56 mol) TOTM-I (1,2,4-tri(2-ethylhexyl) benzenetricarboxylic acid ester) were added. The hydrogenation was carried out using pure hydrogen at 100° C. and a constant pressure of 200 bar. Hydrogenation was continued until no more hydrogen was taken up (20 h) and the reactor was subsequently vented. The conversion of TOMT-I was 95%. The yield of the corresponding cyclohexanedicarboxylic acid ester was 94%, relative to the total amount of the used TOMT-I.

Example 13

In a 300 ml pressure reactor, 10 g of the supported Ru catalyst were placed in a catalyst basket insert and 150 g (0.32 mol) Linplast 68-TM (1,2,4-tri(linear $C_{6-8}$-alkyl) benzoltricarboxylic acid ester) were added. The hydrogenation was carried out using pure hydrogen at a temperature of 120° C. and a constant pressure of 200 bar. Hydrogenation was continued until no more hydrogen was taken up (11 h) and the reactor was subsequently vented. The conversion of Linplast 68-TM was 100%. The yield of the corresponding cyclohexanedicarboxylic acid ester was 99.2%, relative to the total amount of the used Linplast 68-TM.

Example 14

A vertical high-pressure tube made of steel having an inner diameter of 30 mm and a length of 2.2 m was filled with 1.4 l of the supported Ru catalyst. In the slurry process, 0.45 kg/h Palatinol N (CAS No. 28553-12-0) were pumped together with pure hydrogen from the bottom to the top through the reactor at an average temperature of 125° C. and a pressure of 200 bar. After leaving the high-pressure reactor, part of the reaction product was reintroduced into the reactor together with new Palatinol N, while the residual reaction product was vented in a container. The hydrogenation was carried out with a 20% excess of the theoretically required hydrogen while controlling the spent gas. Gaschromatographic analysis of the reaction product showed that Palatinol N has been reacted to an extent of 99.5%. The corresponding cyclohexanedicarboxylic acid ester was obtained with a selectivity of 99.2%. In order to remove the remaining 0.5% Palatinol from the reaction product, the same was pumped through the reactor from the bottom to the top in an amount of 1 kg/h, and the product was vented in a container. The addition of hydrogen was continued as described above. Subsequently, no Palatinol N was found in the product. The selectivity with respect to the corresponding cyclohexanedicarboxylic acid ester after the second hydrogenation was 99%. As side components, about 1% low boiling components (components having a lower boiling point compared to cyclohexanedicarboxylic acid ester) were found. These components were reduced by means of a vapor distillation at 170° C. and a pressure of 50 mbar. The product consisted after this work-up of 99.7% cyclohexanedicarboxylic acid ester.

We claim:

1. A process for hydrogenating a benzenepolycarboxylic acid or a derivative thereof to the corresponding cyclohexane polycarboxylic acid or a mixture of two or more thereof by bringing the benzenepolycarboxylic acid or the derivative thereof or the mixture of two or more thereof into contact with a hydrogen-containing gas in the presence of a catalyst which comprises as active metal at least one metal of transition group VIII of the Periodic Table alone or together with at least one metal of transition group I or VII of the periodic table applied to a support which contains macropores having a pore diameter of greater than 50 nm according to the definition in Pure Applied Chemistry 45, p. 79 (1976) with the proviso that if dimethyl terephthalate is hydrogenated, the hydrogenation using a catalyst which comprises as active metal ruthenium either alone or together with at least one metal of transition group I, VII or VIII of the Periodic Table applied to a support, where the support has a mean pore diameter of at least 50 nm and a BET surface area of at most 30 m$^2$/g and the amount of the active metal is from 0.01 to 30% by weight, based on the total weight of the catalyst, and the ratio of the surface areas of the active metal and the catalyst support is less than 0.05, and/or a catalyst which comprises as active metal ruthenium either alone or together with at least one metal of transition group I, VII or VIII of the Periodic Table in an amount of from 0.01 to 30% by weight, based on the total weight of the catalyst, applied to a support, where from 10 to 50% of the pore volume of the support is formed by macropores having a pore diameter in the range from 50 nm to 10,000 nm and from 50 to 90% of the pore volume of the support is formed by mesopores having a pore diameter in the range from 2 to 50 nm, where the sum of the pore volumes adds up to 100%, is excluded.

2. A process as defined in claim 1, wherein the catalyst comprises as active metal at least one metal of transition group VIII of the Periodic Table either alone or together with at least one metal of transition group I or IV of the Periodic Table applied to a support, where the support has a mean pore diameter of at least 50 nm and a BET surface area of at most 30 m$^2$/g and the amount of the active metal is from 0.01 to 30% by weight, based on the total weight of the catalyst.

3. A process as defined in claim 1, wherein the catalyst comprises as active metal at least one metal of transition group VIII of the Periodic Table either alone or together with at least one metal of transition group I or VII of the Periodic Table in an amount of from 0.01 to 30% by weight, based on the total weight of the catalyst, applied to a support, where from 10 to 50% of the pore volume of the support is formed by macropores having a pore diameter in the range from 50 nm to 10,000 nm and from 50 to 90% of the pore volume of the support is formed by mesopores having a pore diameter in the range from 2 to 50 nm, where the sum of the pore volumes adds up to 100%.

4. A process as defined in claim 1, wherein the catalyst comprises as active metal at least one metal of transition group VIII of the Periodic Table either alone or together with at least one metal of transition group I or VII of the Periodic Table in an amount of from 0.01 to 30% by weight, based on the total weight of the catalyst, applied to a support, where the support has a mean pore diameter of at least 0.1 im and a BET surface area of at most 15 m$^2$/g.

5. A process as defined in claim 1, wherein the benzenepolycarboxylic acid or the derivative thereof is selected from the group consisting of monoalkyl and dialkyl esters of phthalic acid, terephthalic acid and isophthalic acid, monoalkyl, dialkyl and trialkyl esters of trimellitic acid, trimesic acid and hemimellitic acid, monoalkyl, dialkyl, trialkyl and tetraalkyl esters of pyromellitic acid, where the alkyl groups can be linear or branched and each have from 3 to 18 carbon atoms, anhydrides of phthalic acid, trimellitic acid and hemimellitic acid, pyromellitic dianhydride and mixtures of two or more thereof.

6. A process as defined in claim 2, wherein the benzenepolycarboxylic acid or the derivative thereof is selected from the group consisting of monoalkyl and dialkyl esters of phthalic acid, terephthalic acid and isophthalic acid, monoalkyl, dialkyl and trialkyl esters of trimellitic acid, trimesic acid and hemimellitic acid, monoalkyl, dialkyl, trialkyl and tetraalkyl esters of pyromellitic acid, where the alkyl groups can be linear or branched and each have from 3 to 18 carbon atoms, anhydrides of phthalic acid, trimellitic acid and hemimellitic acid, pyromellitic dianhydride and mixtures of two or more thereof.

7. A process as defined in claim 3, wherein the benzenepolycarboxylic acid or the derivative thereof is selected from the group consisting of monoalkyl and dialkyl esters of phthalic acid, terephthalic acid and isophthalic acid, monoalkyl, dialkyl and trialkyl esters of trimellitic acid, trimesic acid and hemimellitic acid, monoalkyl, dialkyl, trialkyl and tetraalkyl esters of pyromellitic acid, where the alkyl groups can be linear or branched and each have from 3 to 18 carbon atoms, anhydrides of phthalic acid, trimellitic acid and hemimellitic acid, pyromellitic dianhydride and mixtures of two or more thereof.

8. A process as defined in claim 4, wherein the benzenepolycarboxylic acid or the derivative thereof is selected from the group consisting of monoalkyl and dialkyl esters of phthalic acid, terephthalic acid and isophthalic acid, monoalkyl, dialkyl and trialkyl esters of trimellitic acid, trimesic acid and hemimellitic acid, monoalkyl, dialkyl, trialkyl and tetraalkyl esters of pyromellitic acid, where the alkyl groups can be linear or branched and each have from 3 to 18 carbon atoms, anhydrides of phthalic acid, trimellitic acid and hemimellitic acid, pyromellitic dianhydride and mixtures of two or more thereof.

9. A process as defined in claim 1, wherein the support comprises activated carbon, silicon carbide, aluminum oxide, silicon dioxide, titanium dioxide, zirconium dioxide, magnesium oxide, zinc oxide or a mixture of two or more thereof.

10. A process as defined in claim 2, wherein the support comprises activated carbon, silicon carbide, aluminum oxide, silicon dioxide, titanium dioxide, zirconium dioxide, magnesium oxide, Zinc oxide or a mixture of two or more thereof.

11. A process as defined in claim 3, wherein the support comprises activated carbon, silicon carbide, aluminum oxide, silicon dioxide, titanium dioxide, zirconium dioxide, magnesium oxide, zinc oxide or a mixture of two or more thereof.

12. A process as defined in claim 4, wherein the support comprises activated carbon, silicon carbide, aluminum oxide, silicon dioxide, titanium dioxide, zirconium dioxide, magnesium oxide, zinc oxide or a mixture of two or more thereof.

13. A process as defined in claim 1, wherein the hydrogenation is carried out in the presence of a solvent or diluent.

14. The process of claim 1, wherein the hydrogenation is carried out continuously.

15. The process of claim 2, wherein the support comprises activated carbon, silicon carbide, aluminum oxide, silicon dioxide, titanium dioxide, zirconium dioxide, magnesium oxide, zinc oxide or a mixture of two or more thereof.

16. The process claim 3, wherein the support comprises activated carbon, silicon carbide, aluminum oxide, silicon dioxide, titanium dioxide, zirconium dioxide, magnesium oxide, zinc oxide or a mixture of two or more thereof.

17. The process claim 4, wherein the support comprises activated carbon, silicon carbide, aluminum oxide, silicon dioxide, titanium dioxide, zirconium dioxide, magnesium oxide, zinc oxide or a mixture of two or more thereof.

18. A plastics product containing a cyclohexanedicarboxylic ester according to claim 12 or a cyclohexanetricarboxylic ester or a mixture of two or more thereof as a plasticizer.

19. A plastics product containing a cyclohexanedicarboxylic ester according to claim 3 or a cyclohexanetricarboxylic ester or a mixture of two or more thereof as a plasticizer.

20. A plastics product containing a cyclohexanedicarboxylic ester according to claim 4 or a cyclohexanetricarboxylic ester or a mixture of two or more thereof as a plasticizer.

21. A plastics product containing a cyclohexanedicarboxylic ester according to claim 1 or a cyclohexanetricarboxylic ester or a mixture of two or more thereof as a plasticizer.

* * * * *

UNITED STATES PATENT AND TRADEMARK OFFICE
CERTIFICATE OF CORRECTION

PATENT NO. : 6,284,917 B1
APPLICATION NO. : 09/581843
DATED : January 1, 2008
INVENTOR(S) : Brunner et al.

It is certified that error appears in the above-identified patent and that said Letters Patent is hereby corrected as shown below:

Col. 4, line 7 incorrectly recites:
"dicyclohexyl trimellitate and trimellitate"

Please replace with:
"dicyclohexyl trimellitate and trimethyl trimellitate"

Signed and Sealed this

Nineteenth Day of May, 2009

JOHN DOLL
*Acting Director of the United States Patent and Trademark Office*

(12) EX PARTE REEXAMINATION CERTIFICATE (4896th)
United States Patent
Brunner et al.

(10) Number: US 6,284,917 C1
(45) Certificate Issued: Jan. 20, 2004

(54) METHOD FOR HYDROGENATING BENZENE POLYCARBOXYLIC ACIDS OR DERIVATIVES THEREOF BY USING A CATALYST CONTAINING MACROPORES

(75) Inventors: Melanie Brunner, Schifferstadt (DE); Arnd Böttcher, Frankenthal (DE); Boris Breitscheidel, Limburgerhof (DE); Klaus Halbritter, Heidelberg (DE); Jochem Henkelmann, Mannheim (DE); Lucien Thil, Limburgerhof (DE); Rolf Pinkos, Dürkheim (DE)

(73) Assignee: BASF Aktiengesellschaft, Ludwigshafen (DE)

Reexamination Request:
No. 90/006,353, Aug. 13, 2002

Reexamination Certificate for:
Patent No.: 6,284,917
Issued: Sep. 4, 2001
Appl. No.: 09/581,843
Filed: Jun. 19, 2000

(22) PCT Filed: Dec. 18, 1998
(86) PCT No.: PCT/EP98/08346
§ 371 (c)(1),
(2), (4) Date: Jun. 19, 2000
(87) PCT Pub. No.: WO99/32427
PCT Pub. Date: Jul. 1, 1999

(30) Foreign Application Priority Data

Dec. 19, 1997 (DE) .......................................... 197 56 913
Jul. 16, 1998 (DE) .......................................... 198 32 088

(51) Int. Cl.⁷ ............................................. C07C 69/74
(52) U.S. Cl. ..................................................... 560/127

(56) References Cited

FOREIGN PATENT DOCUMENTS

DE        2823165        11/1979

*Primary Examiner*—Brian J. Davis

(57) ABSTRACT

A process for hydrogenating a benzenepolycarboxylic acid or a derivative thereof or a mixture of two or more thereof by bringing the benzenepolycarboxylic acid or the derivative thereof or the mixture of two or more thereof into contact with a hydrogen-containing gas is carried out in the presence of a catalyst which comprises as active metal at least one metal of transition group VIII of the Periodic Table alone or together with at least one metal of transition group I or VII of the periodic table applied to a support which contains macropores with the proviso that if dimethyl terephthalate is hydrogenated, the hydrogenation using a catalyst which comprises as active metal ruthenium either alone or together with at least one metal of transition group I, VII or VIII of the Periodic Table applied to a support, where the support has a mean pore diameter of at least 50 nm and a BET surface area of at most 30 m²/g and the amount of the active metal is from 0.01 to 30% by weight, based on the total weight of the catalyst, and the ratio of the surface areas of the active metal and the catalyst support is less than 0.05, and/or a catalyst which comprises as active metal ruthenium either alone or together with at least one metal of transition group I, VII or VIII of the Periodic Table in an amount of from 0.01 to 30% by weight, based on the total weight of the catalyst, applied to a support, where from 10 to 50% of the pore volume of the support is formed by macropores having a pore diameter in the range from 50 nm to 10,000 nm and from 50 to 90% of the pore volume of the support is formed by mesopores having a pore diameter in the range from 2 to 50 nm, where the sum of the pore volumes adds up to 100%, is excluded, and novel hydrogenation products, obtainable by hydrogenating benzenepolycarboxylic acid (derivatives) as well as their use as plasticizers in plastics.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 3 and 16 are cancelled.

Claims 1, 7, 11 and 19 are determined to be patentable as amended.

Claims 2, 4–6, 8–10, 12–15, 17–18, 20 and 21, dependent on an amended claim, are determined to be patentable.

1. A process for hydrogenating a benzenepolycarboxylic acid or a derivative thereof to the corresponding cyclohexane and polycarboxylic acid or a mixture of two or more thereof by bringing the benzenepolycarboxylic acid or the derivative thereof or the mixture of two or more thereof into contact with a hydrogen-containing gas in the presence of a catalyst which comprises as active metal at least one metal of transition group VIII of the Periodic Table alone or together with at least one metal of transition group I or VII of the periodic table applied to a support which contains macropores having a pore diameter of greater than 50 nm according to the definition in Pure Applied Chemistry 45, p. 79 (1976) *in an amount of from 0.01 to 30% by weight, based on the total weight of the catalyst, applied to a support, where from 10 to 50% of the pore volume of the support is formed by macropores having a pore diameter in the range from 50 nm to 10,000 nm and from 50 to 90% of the pore volume of the support is formed by mesopores having a pore diameter in the range from 2 to 50 nm, where the sum of the pore volumes adds up to 100%* with the proviso that if dimethyl terephthalate is hydrogenated, the hydrogenation using a catalyst which comprises as active metal ruthenium either alone or together with at least one metal of transition group I, VII or VIII of the Periodic Table applied to a support, where the support has a mean pore diameter of at least 50 nm and a BET surface area of at most 30 $m^2/g$ and the amount of the active metal is from 0.01 to 30% by weight, based on the total weight of the catalyst, and the ratio of the surface areas of the active metal and the catalyst support is less than 0.05, and/or a catalyst which comprises as active metal ruthenium either alone or together with at least one metal of transition group I, VII or VIII of the Periodic Table in an amount of from 0.01 to 30% by weight, based on the total weight of the catalyst, applied to a support, where from 10 to 50% of the pore volume of the support is formed by macropores having a pore diameter in the range from 50 nm to 10,000 nm and from 50 to 90% of the pore volume of the support is formed by mesopores having a pore diameter in the range from 2 to 50 nm, where the sum of the pore volumes adds up to 100%, is excluded.

7. A process as defined in claim [3] *1*, wherein the benzenepolycarboxylic acid or the derivative thereof is selected from the group consisting of monoalkyl and dialkyl esters of phthalic acid, terephthalic acid and isophthalic acid, monoalkyl, dialkyl and trialkyl esters of trimellitic acid, trimesic acid and hemimellitic acid, monoalkyl, dialkyl, trialkyl and tetraalkyl esters of pyromellitic acid, where the alkyl groups can be linear or branched and each have from 3 to 18 carbon atoms, anhydrides of phthalic acid, trimellitic acid and hemimellitic acid, pyromellitic dianhydride and mixtures of two or more thereof.

11. A process as defined in claim [3] *1*, wherein the support comprises activated carbon, silicon carbide, aluminum oxide, silicon dioxide, titanium dioxide, zirconium dioxide, magnesium oxide, zinc oxide or a mixture of two or more thereof.

19. A plastics product containing a cyclohexanedicarboxylic ester according to claim [3] *1* or a cyclohexanetricarboxylic ester or a mixture of two or more thereof as a plasticizer.

* * * * *

(12) EX PARTE REEXAMINATION CERTIFICATE (6083rd)
United States Patent
Brunner et al.

(10) Number: US 6,284,917 C2
(45) Certificate Issued: Jan. 1, 2008

(54) METHOD FOR HYDROGENATING BENZENE POLYCARBOXYLIC ACIDS OR DERIVATIVES THEREOF BY USING A CATALYST CONTAINING MACROPORES

(75) Inventors: Melanie Brunner, Schifferstadt (DE); Arnd Böttcher, Frankenthal (DE); Boris Breitscheidel, Limburgerhof (DE); Klaus Halbritter, Heidelberg (DE); Jochem Henkelmann, Mannheim (DE); Lucien Thil, Limburgerhof (DE); Rolf Pinkos, Dürkheim (DE)

(73) Assignee: BASF Aktiengesellschaft, Ludwigshafen (DE)

Reexamination Request:
No. 90/007,606, Jun. 28, 2005

Reexamination Certificate for:
Patent No.: 6,284,917
Issued: Sep. 4, 2001
Appl. No.: 09/581,843
Filed: Jun. 19, 2000

Reexamination Certificate C1 6,284,917 issued Jan. 20, 2004

(22) PCT Filed: Dec. 18, 1998
(86) PCT No.: PCT/EP98/08346
§ 371 (c)(1),
(2), (4) Date: Jun. 19, 2000
(87) PCT Pub. No.: WO99/32427
PCT Pub. Date: Jul. 1, 1999

(30) Foreign Application Priority Data
Dec. 19, 1997 (DE) .......................................... 197 56 913
Jul. 16, 1998 (DE) .......................................... 198 32 088

(51) Int. Cl.
*C07C 51/347* (2006.01)
*C07C 67/303* (2006.01)
*C07C 51/36* (2006.01)
*C07C 67/00* (2006.01)
*C07C 69/75* (2006.01)
*C07C 69/00* (2006.01)
*C08K 5/00* (2006.01)
*C08K 5/12* (2006.01)

(52) U.S. Cl. ...................................................... 560/127
(58) Field of Classification Search ................... 560/127
See application file for complete search history.

(56) References Cited

U.S. PATENT DOCUMENTS

| 3,027,398 | A | 3/1962 | Foohey et al. |
| 3,308,086 | A | 3/1967 | Wartman |
| 3,334,149 | A | 8/1967 | Akin et al. |
| 6,248,924 | B1 | 6/2001 | Ruehl et al. |
| 6,388,149 | B2 | 5/2002 | Ruehl et al. |

FOREIGN PATENT DOCUMENTS

DE A 28 23 165 * 11/1979

OTHER PUBLICATIONS

Abstract of DE–A 28 23 165.*
English translation of DE–A 28 23 165 submitted in 90/006, 353.*

* cited by examiner

*Primary Examiner*—Bennett Celsa

(57) ABSTRACT

A process for hydrogenating a benzenepolycarboxylic acid or a derivative thereof or a mixture of two or more thereof by bringing benzenepolycarboxylic acid or the derivative thereof or the mixture of two or more thereof into contact with a hydrogen-containing gas is carried out in the presence of a catalyst which comprises as active metal at least one metal of transmission group VIII of the Periodic Table alone or together with at least one metal of transition group I or VII of the periodic table applied to a support which contains macropores with the proviso that if dimethyl terephthalate is hydrogenated, the hydrogenation using a catalyst which comprises as active metal ruthenium either alone or together with at least one metal of transition group I, VII or VIII of the Periodic Table applied to a support, where the support has a mean pore diameter of at least 50 nm and a BET surface area of at most 30 $m^2/g$ and the amount of the active metal is from 0.01 to 30% by weight, based on the total weight of the catalyst, and the ratio of the surface areas of the active metal and the catalyst support is less than 0.05, and/or a catalyst which comprises as active metal ruthenium either alone or together with at least one metal of transition group I, VII or VIII of the Periodic Table in an amount of from 0.01 to 30% by weight, based on the total weight of the catalyst, applied to a support, where from 10 to 50% of the pore volume of the support is formed by macropores having a pore diameter in the range from 50 nm to 10,000 nm and from 50 to 90% of the pore volume of the support is formed by mesopores having a pore diameter in the range from 2 to 50 nm, where the sum of the pore volumes adds up to 100%, is excluded, and novel hydrogenation products, obtainable by hydrogenating benzenepolycarboxylic acid (derivatives) as well as their use as plasticizers in plastics.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 3 and 16 were previously cancelled.

Claims 5–8, 11 and 18–21 are cancelled.

Claims 1, 2, 4, 10 and 17 are determined to be patentable as amended.

Claims 9, 12, 13, 14 and 15, dependent on an amended claim, are determined to be patentable.

New claim 22 is added and determined to be patentable.

1. A process for hydrogenating a *derivative of a* benzenepolycarboxylic acid [or a derivative thereof] *or a mixture of two or more thereof* to the corresponding cyclohexane [and] polycarboxylic acid *derivative* or a mixture of two or more thereof by bringing the *derivative of the* benzenepolycarboxylic acid [or the derivative thereof] or the mixture of two or more thereof into contact with a hydrogen-containing gas in the presence of a catalyst [which] *to form the cyclohexane polycarboxylic acid derivative or the mixture of two or more thereof, wherein the catalyst* comprises as active metal at least one metal of transition group VIII of the Periodic Table alone or together with at least one metal of transition group I or VII of the periodic table applied to a support which contains macropores having a pore diameter of greater than 50 nm according to the definition in Pure Applied Chemistry 45, p. 79 (1976) in an amount of from 0.01 to 30% by weight, based on the total weight of the catalyst, applied to a support, where from 10 to 50% of the pore volume of the support is formed by macropores having a pore diameter in the range from 50 nm to 10,000 nm and from 50 to 90% of the pore volume of the support is formed by mesopores having a pore diameter in the range from 2 to 50 nm, where the sum of the pore volumes adds up to 100%

[with the proviso that if dimethyl terephthalate is hydrogenated, the hydrogenation using a catalyst which comprises as active metal ruthenium either alone or together with at least one metal of transition group I, VII or VIII of the Periodic Table applied to a support, where the support has a mean pore diameter of at least 50 nm and a BET surface of at most 30 m²/g and the amount of the active metal is from 0.01 to 30% by weight, based on the total weight of the catalyst, and the ratio of the surface areas of the active metal and the catalyst support is less than 0.05,
and/or
a catalyst which comprises as active metal ruthenium either alone or together with at least one metal of transition group, I, VII or VIII of the Periodic Table in an amount of from 0.01 to 30% by weight, based on the total weight of the catalyst, applied to a support, where from 10 to 50% of the pore volume of the support is formed by macropores having a pore diameter in the range from 50 nm to 10,000 nm and from 50 to 90% of the pore volume of the support is formed by mesopores having a pore diameter in the range from 2 to 50 nm, where the sum of the pore voloumes adds up to 100%, is excluded]

*wherein the derivative of the benzenepolycarboxylic acid is selected from the group consisting of monoalkyl and dialkyl esters of phthalic acid, terephthalic acid and isophthalic acid, monoalkyl, dialkyl and trialkyl esters of trimellitic acid, trimesic acid and hemimellitic acid, monoalkyl, dialkyl, trialkyl and tetraalkyl esters of pyromellictic acid, where the alkyl groups can be linear or branched and each have from 3 to 18 carbon atoms, and mixtures of two or more thereof, and*

*wherein the dialkyl ester of phthalic acid is selected from the group consisting of di-n-propyl phthalate, di-n-butyl phthalate, di-tert-butyl phthalate, diisobutyl phthalate, monoglycol esters of phthalic acid, diglycol esters of phthalic acid, di-n-decyl phthalate, diisodecyl phthalate, di-n-undecyl phthalate, diisododecyl phthalate, di-n-octadecyl phthalate, diisooctadecyl phthalate, di-n-eicosyl phthalate, monocyclohexyl phthalate, dicyclohexyl phthalate.*

2. A process as defined in claim 1, wherein the catalyst comprises as active metal at least one metal of transition group VIII of the Periodic Table either alone or together with at least one metal of transition group I or [IV] *VII* of the Periodic Table applied to a support, where the support has a mean pore diameter of at least 50 nm and a BET surface area of at most 30 m²/g and the amount of the active metal is from 0.01 to 30% by weight, based on the total weight of the catalyst.

4. A process as defined in claim 1, wherein the catalyst comprises as active metal at least one metal of transition group VIII of the Periodic Table either alone or together with at least one metal of transition group I or VII of the Periodic Table in an amount of from 0.01 to 30% by weight, based on the total weight of the catalyst, applied to a support, where the support has a mean pore diameter of at least 0.1 [im] *μm* and a BET surface area of at most 15 m²/g.

10. A process as defined in claim 2, wherein the support comprises activated carbon, silicon carbide, aluminum oxide, silicon dioxide, titanium dioxide, zirconium dioxide, magnesium oxide, [Zinc] *zinc* oxide or a mixture of two or more thereof.

17. The process *of* claim 4, wherein the support comprises activated carbon, silicon carbide, aluminum oxide, silicon dioxide, titanium dioxide, zirconium dioxide, magnesium oxide, zinc oxide or a mixture of two or more thereof.

*22. A process as defined in claim 1, wherein the derivative of the benzenepolycarboxylic acid is selected from the group consisting of di-n-propyl terephthalate, di-n-butyl terephthalate, di-tert-butyl terephthalate, diisobutyl terephthalate, monoglycol esters of terephthalic acid, diglycol esters of terephthalic acid, di-n-octyl terephthalate, diisooctyl terephthalate, mono-2-ethylhexyl terephthalate, di-2-ethylhexyl terephthalate, di-n-nonyl terephthalate, diisononyl terephthalate, di-n- decyl terephthalate, di-n-undecyl terephthalate, diisodecyl terephthalate, diisododecyl terephthalate, di-n-octadecyl terephthalate, diisootadecyl terephthalate, di-n-eicosyl terephthalate, monocyclohexyl terephthalate, dicyclohexyl terephthalate; di-n-propyl phthalate, di-n-butyl phthalate, di-tert-butyl phthalate, diisobutyl phthalate, monoglycol esters of* phthalic acid, diglycol esters of phthalic acid, di-n-decyl phthalate, diisodecyl phthalate, di-n-undecyl phthalate, diisododecyl phthalate, di-n-octadecyl phthalate, diisooctadecyl phthalate, di-n-eicosyl phthalate, monocyclohexyl phthalate, dicyclohexyl phthalate; di-n-propyl isophthalate, di-n-butyl isophthalate, di-tert-butyl isophthalate, diisobutyl isophthalate, monoglycol esters of isophthalic acid, diglycol esters of isophthalic acid, di-n-octyl isophthalate, diisooctyl isophthalate, di-2-ethylhexyl isophthalate, di-n-nonyl isophthalate, diisononyl isophthalate, di-n-decyl isophthalate, diisodecyl isophthalate, di-n-undecyl isophthalate, diisododecyl isophthalate, di-n-octadecyl isophthalate, diisooctadecyl isophthalate, di-n-eicosyl isophthalate, monocyclohexyl isophthalate, dicyclohexyl isophthalate; monomethyl trimellitate, dimethyl trimellitate, diethyl trimellitate, di-n-propyl trimellitate, di-n-butyl trimellitate, di-tert-butyl trimellitate, diisobutyl trimellitate, the monoglycol ester of trimellitic acid, diglycol esters of trimellitic acid, di-n-octyl trimellitate, diisooctyl trimellitate, di-2-ethylhexyl trimellitate, di-n-nonyl trimellitate, diisononyl trimellitate, di-n-decyl trimellitate, diisodecyl trimellitate, di-n-undecyl trimellitate, diisododecyl trimellitate, di-n-octadecyl trimellitate, diisooctadecyl trimellitate, di-n-eicosyl trimellitate, monocyclohexyl trimellitate, dicyclohexyl trimellitate and trimellitate, triethyl trimellitate, tri-n-propyl trimellitate, tri-n-butyl trimellitate, tri-tert-butyl trimellitate, triisobutyl trimmellitate, triglycol esters of trimellitic acid, tri-n-octyl trimellitate, triisooctyl trimellitate, tri-2-ethylhexyl trimellitate, tri-n-nonyl trimellitate, triisododecyl trimellite, tri-n-undecyl trimellitate, triisododecyl trimellitate, tri-n-octadecyl trimellitate, triisooctadecyl trimellitate, tri-n-eicosyl trimelliate and tricyclohexyl trimelliate.

* * * * *